(12) United States Patent
Whaite et al.

(10) Patent No.: US 7,292,907 B2
(45) Date of Patent: Nov. 6, 2007

(54) METHODS AND SYSTEMS FOR MANAGEMENT OF INFORMATION RELATED TO THE APPEARANCE OF AN OBJECT

(75) Inventors: Peter Whaite, Montreal (CA); Pierre-Jules Tremblay, Montreal (CA)

(73) Assignee: Peter Whaite et al., Montreal (CA)

( * ) Notice: Subject to any disclaimer, the term of this patent is extended or adjusted under 35 U.S.C. 154(b) by 552 days.

(21) Appl. No.: 10/682,302

(22) Filed: Oct. 10, 2003

(65) Prior Publication Data

US 2004/0136002 A1   Jul. 15, 2004

Related U.S. Application Data

(63) Continuation of application No. PCT/IB02/02547, filed on Apr. 11, 2002.

(30) Foreign Application Priority Data

Apr. 11, 2001 (CA) .................. 2343672
Feb. 19, 2002 (CA) .................. 2372852

(51) Int. Cl.
G06F 19/00 (2006.01)
(52) U.S. Cl. ..................... 700/159; 356/402
(58) Field of Classification Search ............... 700/159, 700/168, 163, 90; 356/402
See application file for complete search history.

(56) References Cited

U.S. PATENT DOCUMENTS

| | | | |
|---|---|---|---|
| 5,690,486 A * | 11/1997 | Zigelbaum | .............. 433/29 |
| 5,873,814 A | 2/1999 | Adair | |
| 5,961,324 A * | 10/1999 | Lehmann | .............. 433/26 |
| 6,007,332 A * | 12/1999 | O'Brien | .............. 433/26 |
| 6,008,905 A * | 12/1999 | Breton et al. | .............. 356/402 |
| 6,206,691 B1 * | 3/2001 | Lehmann et al. | .............. 433/26 |
| 6,239,868 B1 * | 5/2001 | Jung et al. | .............. 356/73 |
| 6,328,567 B1 * | 12/2001 | Morris et al. | .............. 433/215 |
| 6,384,917 B1 * | 5/2002 | Fradkin | .............. 356/402 |
| 2002/0021439 A1 * | 2/2002 | Priestley et al. | .......... 356/243.5 |

FOREIGN PATENT DOCUMENTS

| | | |
|---|---|---|
| DE | 19809563 A1 | 9/1999 |
| DE | 198 20 632 A1 | 11/1999 |
| WO | WO98/02085 | 1/1998 |
| WO | WO 00/30526 * | 6/2000 |

* cited by examiner

*Primary Examiner*—Leo Picard
*Assistant Examiner*—Chad Rapp
(74) *Attorney, Agent, or Firm*—Ogilvy Renault LLP

(57) ABSTRACT

The present invention provides an improved system for measuring the appearance of an object, that improves upon the prior art systems by employing a digital CMOS camera and a variety of features attendant thereto, provides an improved calibration system, an improved quality control system, an improved tooth whitening system, and an improved crown design system.

31 Claims, 8 Drawing Sheets

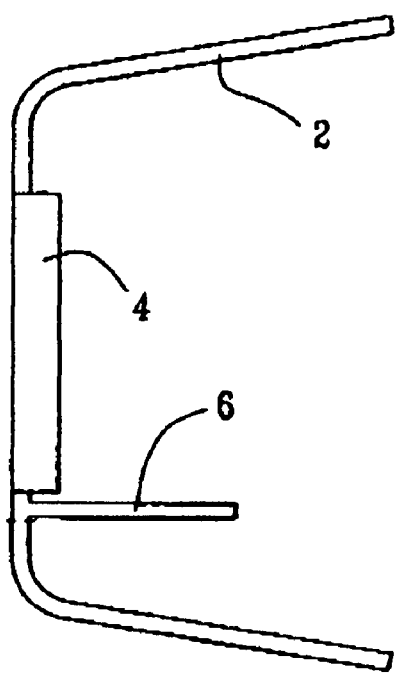
Fig. 4A
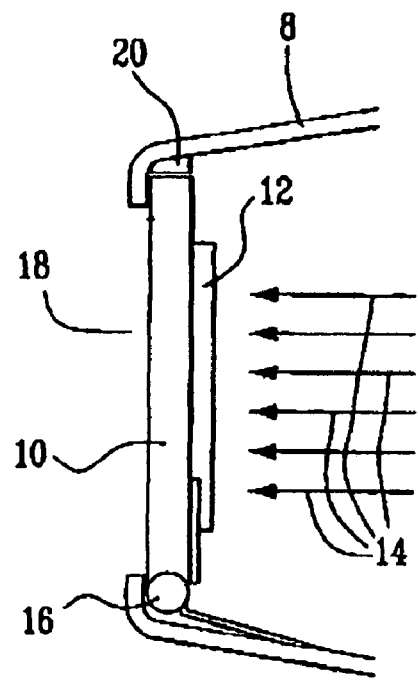
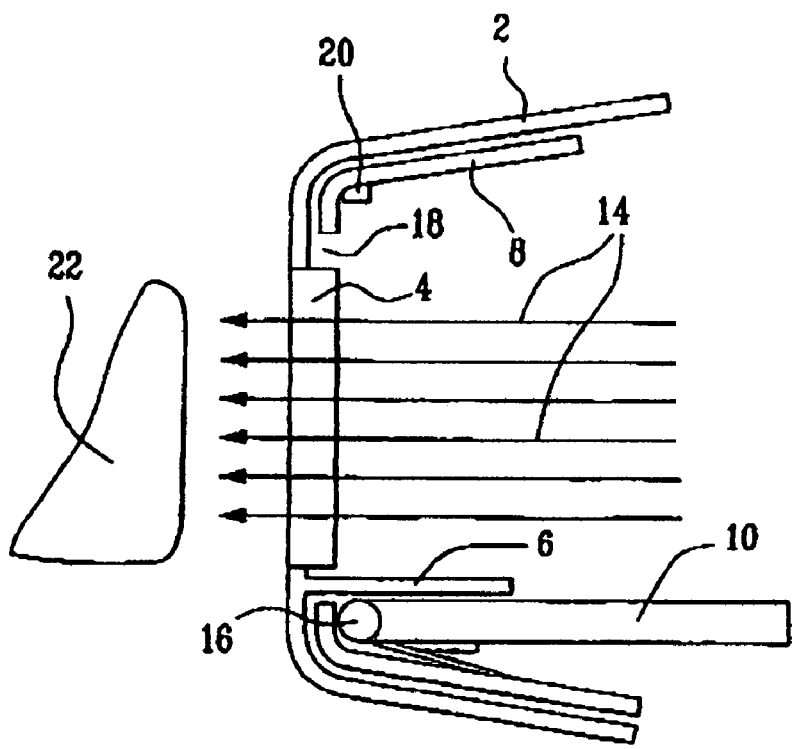
Fig. 4B
Fig. 4C

METHODS AND SYSTEMS FOR MANAGEMENT OF INFORMATION RELATED TO THE APPEARANCE OF AN OBJECT

CROSS-REFERENCE TO RELATED APPLICATIONS

The present application is a continuation of PCT application PCT/IB02/02547 filed on Apr. 11, 2002 designating the United States of America and currently pending.

FIELD OF THE INVENTION

The present invention relates to methods and systems for determining the appearance of an object. More specifically, the present invention relates to methods and systems for managing information related to the appearance of an object. In particularly preferred embodiments, the present invention has application in the field of dentistry.

BACKGROUND OF THE PRESENT INVENTION

The measurement of objects and use of the measurements to manufacture replacement parts substantially identical to the original objects has long been a goal of industry. In the field of dentistry and the methods of making dental prostheses, e.g., crowns, plates and replacement teeth, this has especially been the case. In the early prior art, the methods required a multiplicity of steps, many of which required intervention in the mouth of the patient. Not only was the patient required to attend the dental practitioner a relatively large number of times, but also the intervention frequently was painful, especially during the fitting stages.

For example, in forming a dental crown, the operations included the grinding of the tooth to be replaced in order to obtain a truncated stamp, the taking of an impression of the stump using an elastomer in order to obtain a mold whose hollow part had a shape that was complementary to that of the stump, the casting of plaster into the mold in order to obtain a reproduction of the stump, the preparation of the crown in wax taking into consideration adjacent and antagonistic teeth (a process that was generally highly subjective and the effect of which required high skill and long years of experience by the practitioner), the positioning of the crown in a coating cylinder, the melting out of the wax, the injection of molten metal to replace the wax, stripping and polishing of the metal crown, and the setting of the crown on the stamp.

In spite of the fact that these numerous operations were carried out by highly skilled dental practitioners, in many cases the prosthesis was then required to be further modified after the initial formation. Because of the large number of steps that were involved, and the fact that even with mechanical impressions accurate fits could not be ensured, and because the relationship of each prosthesis to the adjacent and antagonistic teeth had to be gauged subjectively by the practitioner, the production of a dental prosthesis rarely could be accomplished without many visits to the practitioner for further modifications. Moreover, despite the numerous fitting visits and modifications, the danger that the finished prosthesis would cause discomfort to the patient remained.

Other disadvantages of the early dental prosthesis methods included the use of metals as the material for many dental prostheses. For example, the metals used had to be fluid or malleable at easily obtainable temperatures. The numerous steps required the intervention of a laboratory and skilled practitioners at different stages in addition to a dental surgeon. The equipment, including an oven, sand-blasting machine, and inserting equipment, contributed significantly to the cost of producing the prosthesis.

Because of these many disadvantages, improvements in the prior art were sought to overcome these disadvantages. In certain prior art methods, computer aided design principles were employed to attempt to overcome the drawbacks of the prior art See, for example, Duret et al., U.S. Pat. No. 4,663,720 and Duret, U.S. Pat. No. 5,092,022.

Other advances in the state of the art have included improvements regarding the optical characteristics and color of the teeth. See, for example, Jung et al., U.S. Pat. No. 5,880,826 and Breton et al., U.S. Pat. No. 6,008,905. However, despite the advances of the prior art there still exists a need in the art for method and systems that would allow for further management of information related to the appearance of an object such as teeth.

For example, the system described in Breton et al., U.S. Pat. No. 6,008,905 relies on a CCD-based video camera for imaging the patient's tooth. The image is then signalled to the controller, which is in fact a computer system responsible for digitizing, processing and storing the image data. Although this system has been suitable in the past, it suffered from the problem of insufficient storage. Because the signal produced by the camera was not suitable for direct storage on digital medium, it was required to first process the signal. Thus, it would represent a significant advance in the state of the art if an MAT system were to be developed that was not required to employ a video-based camera for imaging the patient's tooth.

SUMMARY OF THE INVENTION

The different methods and systems for managing information related to the appearance of an object in accordance with the present invention are described below in the context of dentistry. However, the present invention applies to the appearance of other objects, and it is believed that a person of ordinary skill in the art can design such systems and methods for applications in other contexts based on the following disclosure.

It is an object of the present invention to provide a system for measuring the appearance of a tooth (hereinafter referred to as the "MAT System").

It is also an object of the present invention to provide a MAT system that is based on an embedded system design, allowing the MAT device to take the form of a handheld device.

It is another object of the present invention to provide for connection of a MAT system to a computer network, such as the Internet.

It is a further object of the present invention to provide a method for calibrating a MAT system.

It is still another object of the present invention to provide a method for using the MAT system in the quality control of direct and indirect dental restorations.

It is a still further object of the present invention to provide for managing information related to bleaching a patient's tooth with the MAT system.

It is a further object of the present invention to provide a system to assist laboratories in designing crowns, to provide a system for modifying the three-dimensional model of a tooth, and to provide a system for determining a recipe for building a particular prosthesis.

These and other objects are met by the present invention that is described in more detail below.

BRIEF DESCRIPTION OF THE DRAWINGS

FIGS. 4A-4C show a preferred embodiment of a calibration attachment and how the calibration attachment fits over the nose of an MAT device in accordance with the present invention.

DETAILED DESCRIPTION OF THE PRESENT INVENTION

Figure 1:
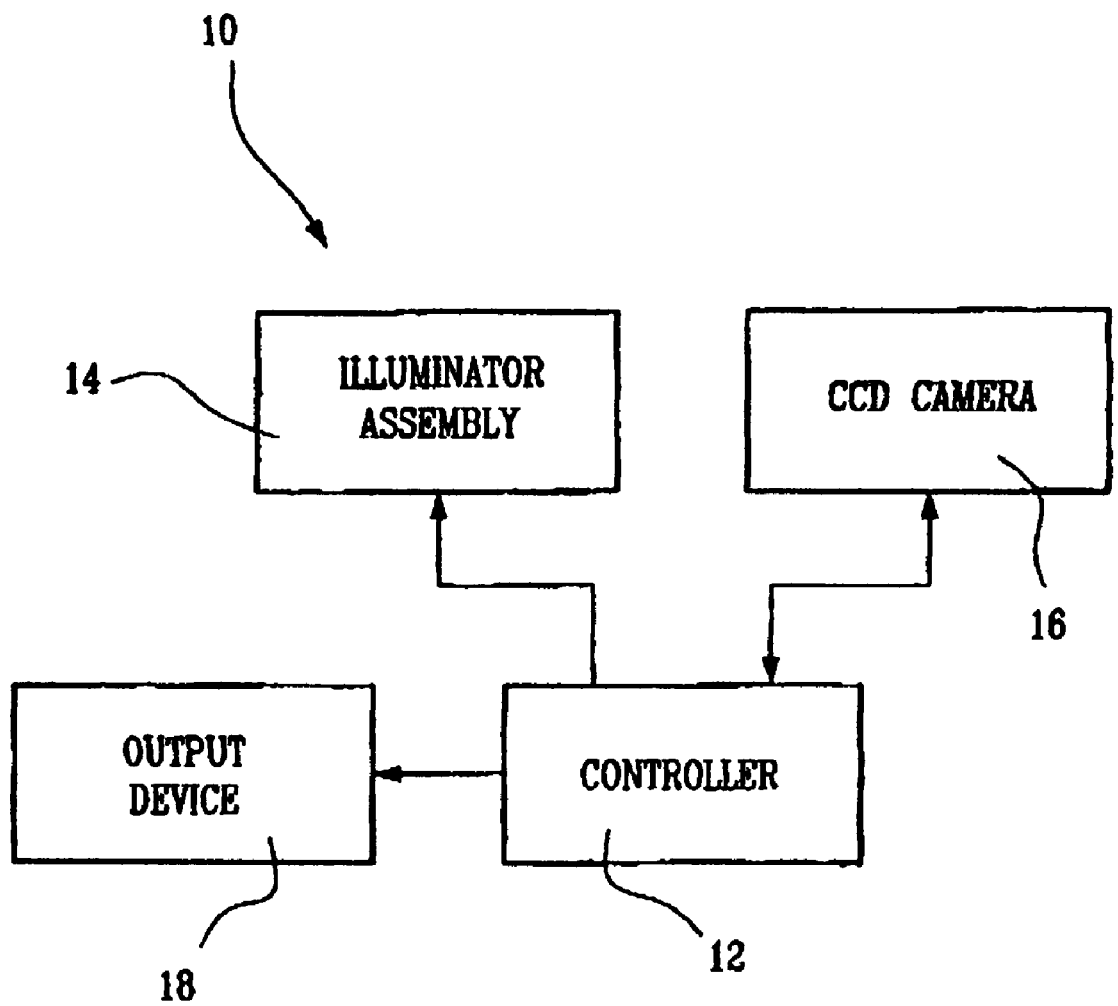
FIG. 1 is a flow chart showing the basic system of the device of U.S. Pat. No. 6,008,905.

System to Measure the Appearance of an Object: According to one aspect of the present invention there is provided a system and apparatus for measuring the appearance of a tooth (the "MAT System"). The MAT system is an embedded system design, is advantageously in the form of a handheld device and includes the following elements:

A light sensitive device such as a CCD or CMOS sensor for capturing the image of a patient's tooth, the sensor preferably being in the form of a Complementary Metal-Oxide-Silicon (CMOS) device, or other sensor known to those skilled in the an. Also contemplated is the sensor described in U.S. Pat. No. 5,965,875, sometimes referred to as Foveon's X3 technology and is based on sensors using the color separation properties of silicon.

A memory storage system for saving the captured images.

A display device on the handpiece to display output to the user, such as the captured image, preferably in the form of an LCD panel, the LCD panel also preferably being able to display interpretive maps such as paint-by-number maps displaying the information from the sensor.

An internal CPU, preferably provided with firmware (i.e., software stored in non-volatile memory), for processing signals from the sensor and other inputs or outputs to the system and allowing interpretation and processing of images in the central memory, thus allowing the device to operate independently from a computer. Exemplary of a suitable system is the system described in the Figures of U.S. Pat. No. 6,008,905. Although in the '905 patent, the charged coupled device "CCD") camera is described as residing in the "camera head," the controller is typically a computer processor and the output device is typically computer memory. In the present invention, however, the CCD camera, controller and certain aspects of the output device (such as removable and non-removable memory) all reside in the camera head Furthermore, there is no separation between the CMOS sensor, controller and memory; they are all part of the camera. In especially preferred embodiments, the internal CPU is also provided with either re-programmable memory (e.g. EEPROM) or non-volatile memory (e.g. NVRAM) enabling the firmware of the device to be changed and enhanced if desired.

a means for transferring stored image data to a remote systems, for example a floppy disk, flash card, etc.

a software program, operating system, stored in machine code form in the embedded system's non-volatile memory, which operates the various modules mentioned above.

The present invention is an improvement on the invention disclosed in U.S. Pat. No. 6,008,905, which is incorporated herein by reference in its entirety. In U.S. Pat. No. 6,008,905 and system for obtaining measurement of the appearance of an object is described with the use of a CCD-based video camera. The CCD-based video camera previously employed was a typical electronic camera comprising an electronic photosensitive color array (the sensor) that captures light on a two-dimensional area in the form of electric charge. The light-sensitive component captures light continuously, therefore a shutter (mechanical or electronic) was used to create and transfer names that correspond to a single image. Typically, the camera assembly also included optics (an objective lens) and electronics to convert the electrically-charged array (image data) into a signal that can be conveyed to a computer, VCR, television or other processing, storage or display device. The computer system used to process the captured images was external to the camera assembly.

The present invention provides an improvement on this system by providing a digital camera platform. In the digital platform of the present invention, the computer system is embedded into the camera design so that the signal coming from the camera can be immediately converted to a format suitable for digital storage and processing. Thus, the digital camera platform of the present invention is an embedded system that is specialized for processing the signal coming from an electronic imaging sensor. Digital camera platforms are available commercially from manufacturers such as Motorola, Intel, LSI Logic and Sound Vision Inc.

The use of a digital camera platform, such as but not limited to a color CMOS sensor, enables many advantages over the prior art. The present invention applies the digital camera technology platform to the MAT system concept, such as that set forth in U.S. Pat. No. 6,008,905, and also includes other aspects specific to the MAT application, such as, the calibration target-flap, the illumination system, light source feedback, and an application-specific program to run on the processor. Thus, the present invention provides benefits over the prior art MAT systems in the reduction of the physical size of the system, in the calibration and light control processes by having the processor in direct and continuous contact with the light-sensing device, in simplifying the user interface which is tuned to the application instead of having to deal with a general-purpose computer system, and in marketing aspects where the device is viewed by the customer as a single purpose appliance with a finite set of features tuned to this purpose. Further advantages are that voice recordings can be linked to the digital image to describe and annotate the image, keyboard input information can be linked to the digital image to describe and annotate the image and an LCD display can be placed on the unit to display the captured image and also display interpretive maps such as paint-by-number maps showing the information.

Thus referring to FIG. 1 there is shown the flow chart FIG. 1 of U.S. Pat. No. 6,008,905. Referring to FIG. 1, the apparatus 10 is seen to comprise a controller in the form of a computer 12, an illuminator assembly 14, a CCD (Charged Coupled Device) camera 16 and an output device 18. In this device, all of the processing occurs in the controller. The CCD camera is described as residing in the "camera head", the controller is a separate computer processor and the output device is separate computer memory. Here however, the CMOS camera, controller and memory are not separated, instead they are all part of the digital camera platform. This enables the advantages of the present invention to be realized In preferred embodiments, the handheld device further comprises one or more of the following elements:

(a) A microphone to record voice information to describe and annotate the patient's tooth, which information can be linked or attached to the appropriate image. Exemplary of annotations that might be recorded are name/coordinates of the dentist, name/coordinates of the patient, name/coordinates of the dental lab, the type of restoration (crown, veneer, bridge, all ceramic crown, porcelain fused to metal crown, etc.), the type of material to be used by dental lab, details of the shape or appearance of the tooth that the dental lab should take note of and pay attention to; and description of patient objectives.

(a) A keypad for inputting textual information about the patient, which information can be linked or attached to the appropriate image.

(b) An internal speaker to play the attached voice annotations.

(c) A source of illumination, such as one using white light emitting diodes (LED) to achieve a field of uniform illumination, and, preferably, wherein the diodes are present inside the device itself making it self illuminating. And/or (d) An attachment to be positioned on the font of the device to alter the illumination pattern and the depth of focus, allowing it to be used as a regular digital camera that can also be used to take fill-face or "smile" images of the patient In order to better build a prosthesis, it is advantageous if the clinician is able to view the context of the tooth, that is, how the looks in the full smile of the patient. Presently, the MAT systems of the prior art, such as that described in U.S. Pat. No. 6,008,905, only allow for measurement of one tooth at a time. The attachment would allow the clinician to use an MAT device to capture an image of the full smile of the patient by clipping onto the "nose" of the MAT handpiece.

Figure 2:
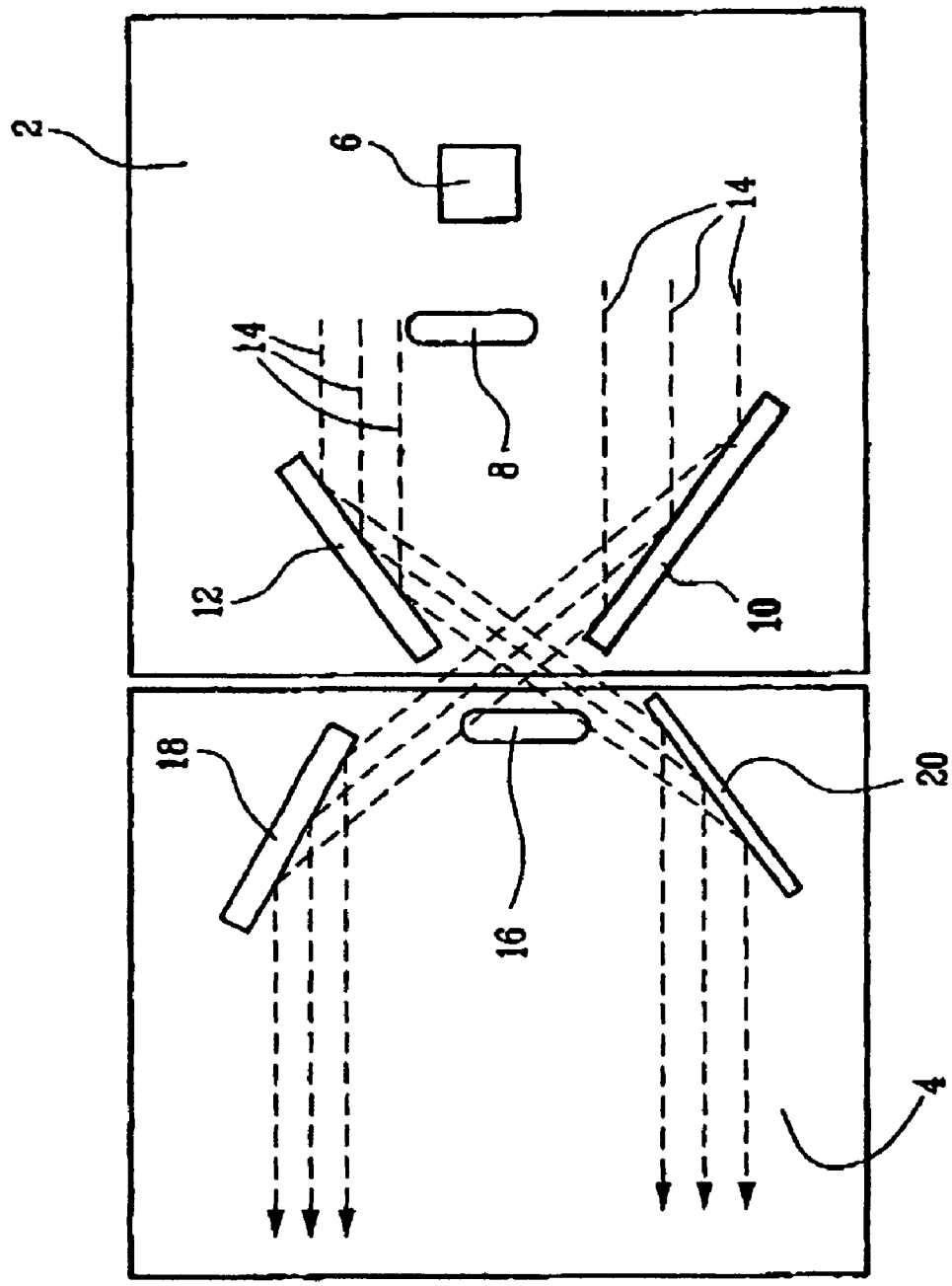
FIG. 2 is a top view showing a preferred embodiment of an attachment that can be used to obtain full smile images for use in accordance with the present invention.

A preferred form of the attachment is shown in FIG. 2, wherein box 2 shows the optical system of the prior art, such as in U.S. Pat. No. 6,008,905. This portion of the device has a sensor 6, a lens 8 and two mirrors 10 and 12 for reflecting light beams 14. Box 4 represents an attachment in accordance with the present invention. Attachment 4 comprises a lens 16 for changing the focal length and two additional mirrors 18 and 20 for redirecting the light beams to illuminate the full smile of the patient 22.

In still another preferred embodiment, the handheld device can be configured to allow its connection and communication to the Internet or another computer network, either by line or remotely, in order to perform one or more of the following functions:

(a) Transfer the information obtained by the device to a dental laboratory. Typically, the dentist sees the patient and uses the device of the present invention to measure the appearance of the tooth. For indirect restorations, it may be necessary for the dental laboratory to fabricate the prosthesis.

Figure 3:
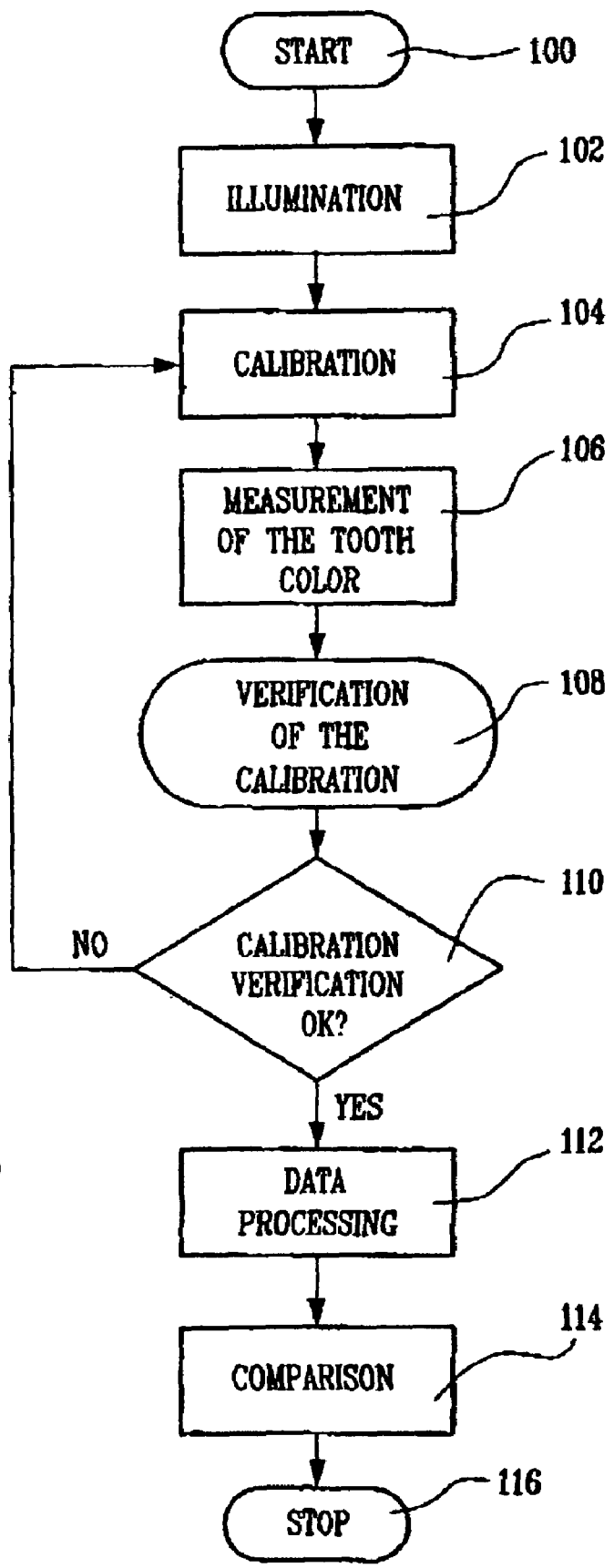
FIG. 3 is a flow chart showing the basic processing steps of an MAT device.

(a) Connect to a central web-site to receive the results of image treatment based on an ASP (application specific portal) model. Image treatment is best understood by referring to FIG. 3 of the present invention, which is similar to FIG. 3 of U.S. Pat. No. 6,008,905. Because, all of the parts of FIG. 1 of U.S. Pat. No. 6,008,905 remain present, albeit in a different and improved format that provides many significant advantages, the flow chart of steps remains the same. Thus, generally the method comprises the following steps performed in sequence: (1) 100—starting the apparatus; (2) 102—illuminating the tooth via a predetermined illumination method; (3) 104—calibrating the MAT device; (4) 106—acquiring data pertaining to the color shade and translucency of the tooth; (5) 108—optionally, verifying that the initial calibration is correct; if not (step 110), returning to step 104; (6) 112—processing the data to produce a color shade image map and a translucency image map; (7) 114—optionally after a duplicate tooth has been made from the data of the color shade and translucency image maps, the image of the duplicate tooth may be acquired by placing the duplicate tooth in place of the original tooth and by performing steps 1 to 5 to yield duplicate color shade image and translucency image maps that may be compared to the original maps to control the quality of the finished product; and (8) 116—stopping the apparatus. The image treatment is typically steps (5) to (8) above. Image treatment can also describe quality control, tooth whitening and restoration recipe embodiments described later. The ASP model may sometimes be required where a dental lab or dentist does not have the complete software for complete image analysis or may require some additional information. In this case the following could occur: take the image with the device of the present invention and download that image to a website. Once the image is downloaded, the user can request reports with specified parameters. For example, the user can request an exact recipe for fabricating an all ceramic crown using material x give a tooth preparation of given parameters and a restoration with x mm of thickness. The web site can then provide the information responsive to the user's request by software running at the central server, by a human expert, specially trained, who can analyze the data and generate the report; or a combination of the two. This function would be especially useful for a user who would prefer to proceed with a pay-per-use model as opposed to a software license or where the software is insufficient by itself and requires a human expert to work along side the software for interpretation of the information.

(b) Connect to a central web-site to receive updates and enhancements to the firmware. And/or (c) Connect to a central web-site to receive regular maintenance checkups and device problem diagnoses. This feature would be effected by the device uploading to a website or any central computer status information, such as log files containing the results of device calibrations (that are conducted with regular frequency to accommodate variations in the sensor and the light source and illumination). This information could show, by way of non-limiting example, that the color balance of the camera is incorrect or if the light bulb is nearing the end of its life and should be changed. The communication would occur as either the website serve querying the device periodically and uploading information stored in the device; or the device periodically downloading information to the website. The latter could occur periodically, or may occur as the result of some diagnoses that is being processed in the device itself Calibration: According to another aspect of the present invention, there is provided a method and apparatus for calibrating a MAT System device. The system of the present invention is a hand-held appearance measurement device. The handpiece consists of optics that focus colluminated light through an exit aperture onto the object to be measured, and a stable image sensor device mounted behind the aperture that captures an image of the object. The image forms the basic data input to image processing algorithms that produce quantifiable appearance measures (color, translucency, etc.) of the object being measured. In order that the image data is reliable and repeatable, the design and construction of the handpiece must fulfill two crucial functions: (i) the sensor in the device must be periodically calibrated by capturing an image of a known calibration target; and (ii) the optics of the device must be protected from contamination by covering the exit aperture in the nose of the handpiece with a transparent window.

Fulfilling these functions has lead to several difficulties, which in turn increases the cost of the instrument. One, the target must be repeatably and accurately positioned in front of the camera. To achieve this the calibration target is mounted in a cradle that locates itself precisely on the nose of the instrument. This in turn requires precise mechanical design and fabrication of both the docking mechanism and the nose piece of the instrument. Two, the target must be kept clean. Because the target is open to allow the handpiece access, it can accumulate dust and dirt. In addition, failing to remove the aseptic shield in front of the handpiece before docking can contaminate the target area. Avoiding these problems complicates the mechanical design. Third, reflection of light from the exit aperture window causes the illumination level to drop. Dust, dirt, and scratches on the front window spoil its optical properties and interfere with the calibration. These problems are solved by the calibration system as described below.

The calibration system of the present invention comprises:

providing a cradle for holding the MAT device, which cradle houses a calibration path of specific design. The cradle is designed to accurately position the calibration target correctly for the MAT device, that is to place it repeatably and accurately in the nominal measurement position of objects normally measured by the device. Typically, the cradle will fit over the nose of the instrument and serves as a table-top or wall-mounted stand when the device is idle. A proximity sensor or switch in either the cradle or the MAT device can be used to automatically start the calibration device when the device is placed in the cradle ("docked") and to stop it when the device is removed ("undocked").

Alternatively, in an especially preferred embodiment, the calibration target can be mounted in a door. With this preferred mechanism the device is provided with a spring loaded door placed over the exit of the handpiece of the device of the present invention. This prevents dust, dirt and biological contaminants from entering the optics. It also removes one layer of glass from the optical path thus avoiding the optical problems inherent in the protective window. The asceptic shield is fabricated with a tongue that pushes the door open when the shield is placed over the nose of the handpiece. This allows the light to escape, thus making it possible to illuminate and image the subject. A calibration target is mounted on the rear of the target door so that when the door is closed, the target is illuminated and can be imaged by the camera, thus permitting a calibration to be taken. Because the target is mounted on a door that is permanently attached to the optics, it is easier to make the mechanics precise and repeatable. Further, a proximity sensor (optical, mechanical or magnetic) is mounted in the handpiece to detect when the door is fully closed. Removing the shield therefore causes the sprig to snap the door shut trigger the proximity sensor and trigger a calibration automatically.

Referring to FIG. 4A there is shown a shield 2 having a window 4 and a tongue 6. FIG. 4B shows the nose 8 of an MAT device. A door 10 blocks opening 18 and is held closed by spring means 16. Attached to the inside of door 10 is a calibration target 12, which is lit with illumination 14. A proximity sensor 20 is positioned on nose 8 to determine if door 10 is closed. In FIG. 4B, the door 10 is close so that proximity sensor 20 is on and the calibration can commence. Referring to FIG. 4C, the shield 2 is placed over the nose 8. Tongue 6 acts to open door 10. Upon opening, proximity sensor 20 is off, disabling calibration, and allowing measurement of object 22 to commence.

(b) providing the calibration process with a sleep mode, such as, for example, providing means for changing the illumination intensity if the unit has not been used for a set period of time. This feature is provided to reduce the light intensity when the unit is not in use. This feature provides at least two benefits, (1) extending the life of the lamp in the illuminator by lowering the operating temperature of the filament; and (2) extending the life of the calibration target by reducing color change caused by exposure to light;

(c) spatial compensation means for known and consistent spatial variations in the image. In order to measure appearance it must be assumed that spatial variations in illumination falling on the object being measured are negligible with respect to measurement error. However, because variation is inevitable, for example because of vignetting, it is often difficult to achieve the low spatial variation needed for precise measurement. Provided the spatial variation is constant through time, it can be measured when the instrument is set up by taking an image of a target of uniform appearance that can be used to compensate during the calibration process. Spatial variation can also occur in the imaging system but the net effect is that it combines with illumination variation. Spatial compensation therefore corrects for the combined spatial variation of both the image and the illumination subsystems;

(d) light feedback control means using, for example, camera output to modify the light source, thereby allowing the system to compensate for variations in both the illumination and imaging subsystems Commercial light feedback control means arc known in the art, such as Illumination Technologies 3900 SmarLite™ with LightLock™. See www.illuminationtech.com) but these would place the feedback sensor at the entrance to the optic fiber bundle used to deliver light to the illumination subsystem. As a result, they cannot compensate for changes in the illumination optics (the fiber bundle, lenses, filters, mirrors, and windows), or for changes in the optics (windows, lenses, filters and sensor). By using the camera itself as the feedback sensor, the feedback control process will adjust the illuminator to provide constant light on the camera sensor, thus compensating for changes in both the illumination and imaging subsystems. A known object, such as the calibration target, must be measured while the light feedback control process is in action;

(e) means for implementing the concept of absolute color standards for inter-device communication. Quantification of appearance requires precise measurement of color. When multiple MAT devices report to a central processing facility, for example when dentists transmit tooth appearance data to a dental laboratory, it is essential that all the devices report the same color when measuring the same object. In practice, however, all devices will measure color differently, so each unit must be individually corrected to compensate for the differences. The problem is solved by having each unit measure an absolute color standard when it is set up, and to transmit the absolute standard with the measurement. With this, the differences between units can be characterized;

(f) process for selecting the reference colors of the calibration standard for (i) natural teeth and shade guides specifically; and (ii) for any range of colors generally. This process generally comprises (1) evaluating the aging properties of the materials used to make the colors. Some materials are known to fade faster than others, e.g., many red dyes are notoriously unstable while some green pigments are very stable. From these a candidate group of colors is selected. (2) From the selected materials, choose colors that encompass all the colors to be measured by the device;

(g) means for signaling need for replacement of calibration color patch, which can fade over time; the means for signaling can be a flag, such as, for example, a patch of color that has a known lifetime substantially less than the calibration colors so that when this patch of color slightly changes color, a warning is issued for the calibration target to be replaced. Alternatively, because different colors change at different rates, then changes in the differences between colors of a calibration target can also signal the need for replacement;

(h) bar codes attached to each calibration patch for identifying the calibration patch uniquely, the codes can be read by a digital camera and transmitted to a central web-site along with the measured calibration colors, thereby allowing calibrations of individual units to be monitored at the central web-site, and for their replacement to be scheduled in a timely manner.

It is noted that the calibration method described above can be used with the MAT system of the present invention, or with other MAT systems known in the prior art. Exemplary of a prior art MAT system is the ShadeScan Systems™ from Cynovad Inc.

Quality Control: In another aspect of the present invention, a method is provided for using a MAT System in the quality control of direct and indirect dental restorations. More specifically, a MAT System, such as the one described above, or the ShadeScan System™ is first used to measure the prosthetic tooth ("prosthesis") in an environment that corresponds to the mouth into which the prosthesis will be placed After the prosthesis is measured, a method for analyzing the prosthesis, as described hereinbelow, is used to assess if the prosthesis matches the adjacent teeth in the mouth. If the prosthesis requires reworking according to the system for analyzing the prosthesis, a method according to the present invention is used to provide information to a practitioner on how to achieve the final result. It is to be noted that the term "practitioner" is intended here to include dentists, dental assistants, dental technicians and any users in a dental office or dental laboratory.

The system for analyzing prosthesis in accordance with the present invention comprises the following elements:

(1) a MAT system;
(2) a processing unit configured to implement a method for analyzing prosthesis according to an embodiment of the present invention;
(3) an input means in the MAT system for allowing the practitioner to detail features of the patient's mouth, for example, size of the patient's arch, color of gums, spacing between teeth and other relevant features;
(4) a mouth modeler, that is a mount to mimic the optical and appearance properties of a canonical human mouth. The appearance of a natural tooth or a restoration is dependent on its environment, that is, the neighboring teeth and gums. Therefore, a prosthetic tooth will appear (both to the human eye and the MAT system) different depending on whether it is viewed in isolation outside of the mount, or if it is viewed in position within the oral cavity. Thus, the role of the "mouth modeler" is to provide an environment where one can measure the prosthesis and the measurement would be a valid estimate of what the restoration would look like once it is fixed within the mouth. The mouth modeler is contemplated to be either physical or virtual where the user inputs the parameters of the mouth description. The mouth modeler preferably includes one or more of the following features:
(i) size and shape of the canonical mouth, lips and associated oral cavity having the optical properties to match the human mouth; it also preferably allows for varying the properties of the model according to the features displayed by the MAT System;
(ii) artificial gums that mimic the color and translucence of natural canonical gums;
(iii) prosthetic teeth that are removable with a bottom and upper DA arch of the mouth into which prosthetic teeth can be inserted; wherein there is also provided a multiplicity of prosthetic teeth having varying appearance, color, translucency, shape and morphology from which the practitioner can choose. By having the prosthetic teeth be removable they can be placed in the mouth modeler for quality control, and so a prosthesis for a particular tooth can be placed in the proper anatomical location in the mouth modeler;
(iv) ability to allow the practitioner to place the prosthesis into the mouth modeler and to measure the results using the appearance measuring device.

Once the image is captured, the system software will be able to analyze a method including the following steps:

(a) displaying the original image of the tooth (or teeth if more than one was used as the prototype tooth);
(b) deforming or morphing the original teeth from which the prosthesis is built into the same shape as the prosthetic tooth;
(c) measuring the appearance of the prosthetic tooth using the mouth modeler;
(d) comparing the appearance, including factors such as color or shade and translucency of the original tooth with the prosthetic tooth, via a displayed map using a metric, such as the CIELab standard ΔE (Commission Internationale de l'Éclairage) that measures the difference between two colors;
(e) verifying if the prosthesis is acceptable using a multiplicity of predetermined criteria, such as the price of the prosthesis, ΔE, materials available, aesthetics required, patient preferences, type of restoration, physical constraints to the fabrications such as thickness available, etc., and (f) providing information on how to remake the prosthesis, such that the final result would be acceptable. This would include which areas of the prosthesis to remove, which materials to use, in what combinations, and how to use them.

Figure 5:
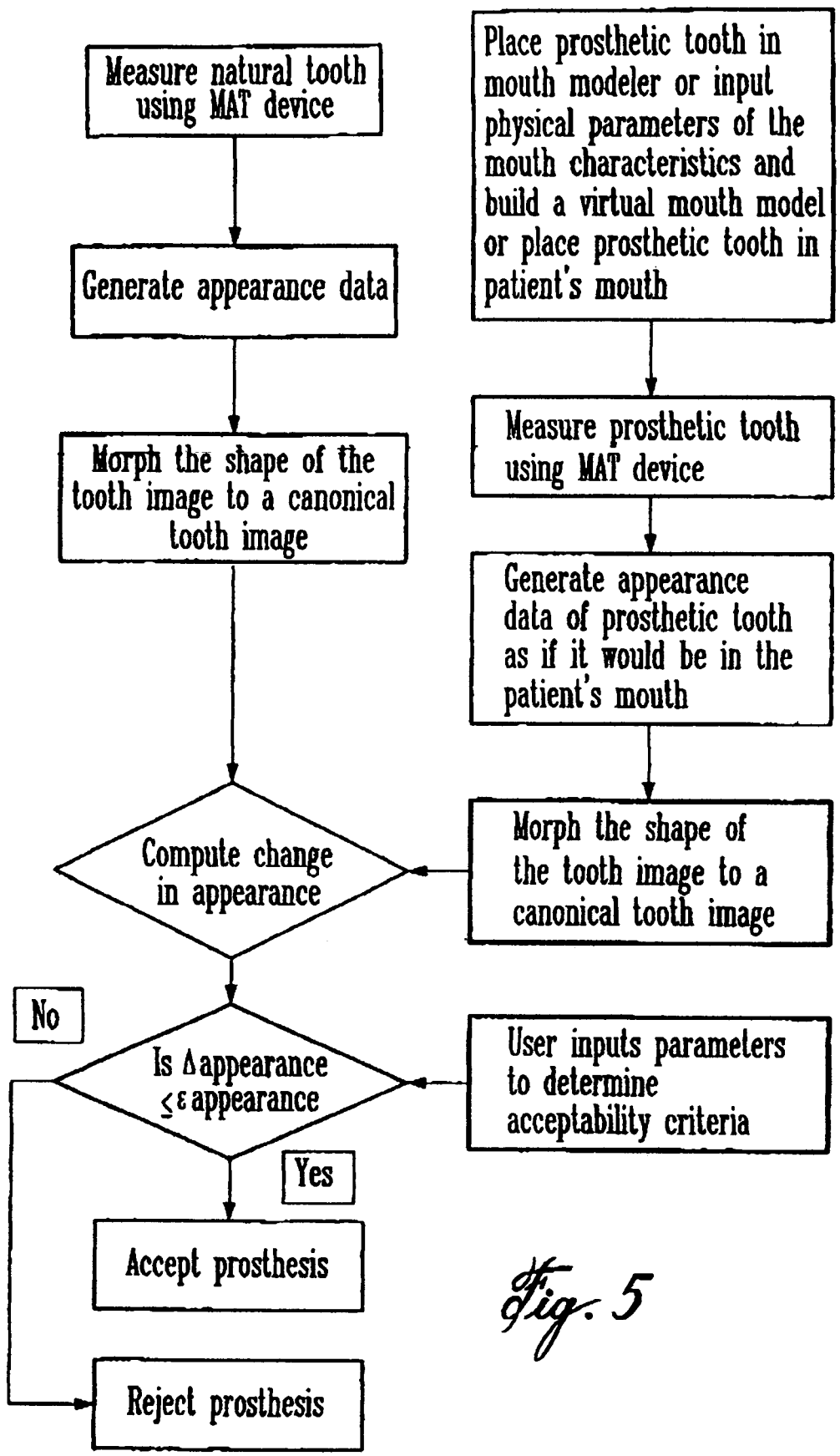
FIG. 5 is a flow chart outlining a preferred quality control aspect of the present invention.

Referring to FIG. 5 there is provided a flow chart of the quality control aspects of the present invention. As shown in FIG. 5, the appearance of the natural tooth over its surface, i.e., its color and translucency, is measured in a MAT device. From that measurement, appearance data is generated in the CPU of the MAT device. The color is determined according to methods known to those skilled in the art such as HVC color space, RGB color space, CIELAB color space or another similar color space measurement. The translucency is measured according to methods known to those skilled in the art, such as the method described in U.S. Pat. No. 6,008,905. After generating the appearance data, the data is adjusted to correlate to a canonical tooth image. In parallel, the prosthetic tooth is placed in a mouth modeler, or directly into the patient's mouth, or a virtual tooth model is built based on inputted parameters of the patient's mouth characteristics, and the prosthetic tooth is measured in a MAT device for color and translucency. The measurements are then used to generate data of the prosthetic tooth as it would appear in the patient's mouth, and the appearance data is adjusted to a canonical tooth image. The canonical tooth image shape can be equivalent to the image shape of the restoration.

The adjusted data from both the natural tooth and the prosthetic tooth are then compared to compute the $\Delta$ appearance. The $\Delta$ appearance is the metric quantifying the difference between the appearance of the natural tooth and the appearance of the prosthetic tooth. This metric is a function of color and translucency over the whole surface of the tooth. The $\Delta$ appearance is then compared to the $\epsilon$ appearance, which are the satisfaction criteria to determine if the appearance of the natural tooth and the prosthetic tooth are perceptually significant over the whole surface of the tooth. This function also has parameters that are input by the user. These are dependent on cost, acceptability, type of restoration, physical restraints, etc. If the $\Delta$ appearance meets the appearance criteria, then the prosthesis is acceptable, and if not, the prosthesis is rejected.

Tooth Whitening: In still another aspect of the present invention, a method is provided for managing information related to whitening or bleaching a patient's tooth, for use with a MAT system such as the ShadeScan System™. The method of this aspect of the present invention comprises:

(a) displaying to a patient a palette of colors that correspond to a range of shades of natural teeth and allowing the patient to select the shade that the patient feels most closely corresponds to the shade of the patient's teeth. This information is then entered into a computer connected to the MAT system;

(b) using a MAT system to determine the shade pattern of the patient's teeth; preferably the MAT system of the present invention;

(c) displaying three images on the MAT;
  (1) the original image obtained by the MAT system and shade map of the patient's actual tooth;
  (2) an image of the patient's tooth (and its corresponding shade map) as it is perceived to be, i.e., the tooth image processed as it would appear with the selected shade;
  (3) an image of the patient's tooth (and its corresponding shade map) as predicted, for example, by a MAT system after a tooth whitening procedure. This information is derived from the knowledge management aspects of the MAT system Preferably this information is displayed via a comparison map that: compares the appearance of the tooth before and after whitening via a map using a metric, such as the metric CIELab standard $\Delta E$; and compares the appearance of the tooth before whitening with the system's predicted results of the whitening via a map using a metric, such as the metric CIELab standard $\Delta E$, (4) optionally presenting a series of images as described above predicting the progress of the whitening procedure at each scheduled appointment, thus allowing patients to see the projected progression of the treatment.

The above information can then be used by the practitioner to teach and explain the tooth whitening process to a patient. The patient will better understand what to expect after each whitening treatment and how fixture treatments will impact the whitening process. As the patient undergoes the tooth whitening process, the above information managing method can also provide the practitioner with a clear mechanism to append new MAT images to the patient's history. This information obtained also can then be optionally downloaded onto a dedicated web site. The information collected at that web site then could be used to refine the tooth whitening model. The tooth whitening model may be incorporated into an expert system that could be used to advise the dentist of the optimal whitening treatment.

At the end of the treatment, the information managing system may further provide a history of the tooth whitening process as well as details on the progression of whitening over a period of time. This can be used to show the patient the changes that have occurred and can also be used by the practitioner to better understand the whitening procedure for use in furniture cases.

The goal of the tooth whitening aspect of the present invention to aid the dentist in discussing the benefits of a tooth whitening procedure, and to enable the dentist to predict the resulting appearance of a tooth after a whitening procedure. Also, it can be used as a reference tool to track the shade of a patient's tooth over time. A tooth gets whiter immediately after a tooth whitening procedure but progressively darker over time, such that a subsequent whitening procedure may be necessary.

Figure 6:
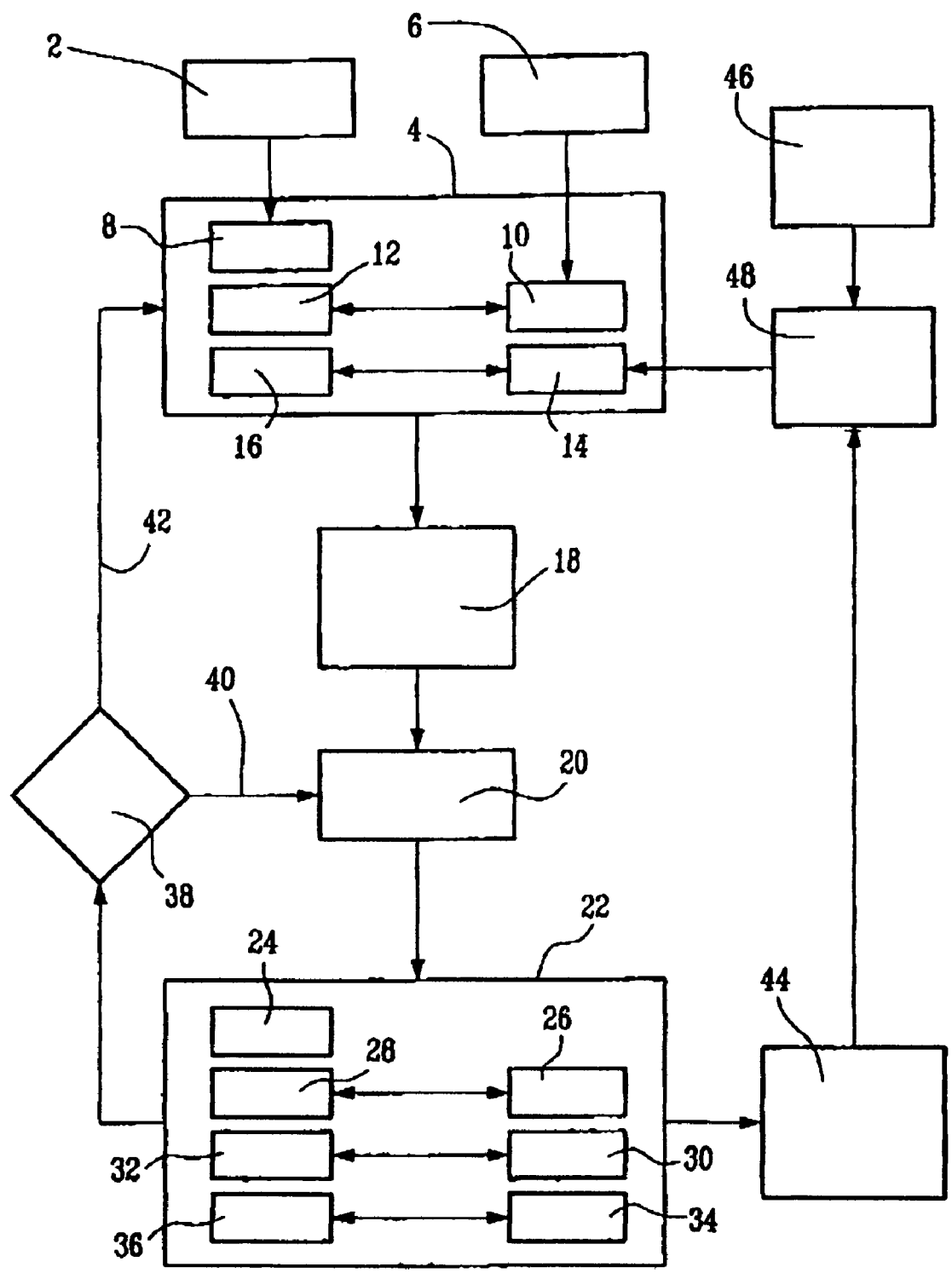
FIG. 6 is a flow chart outlining a preferred tooth whitening aspect of the present invention.

Referring to FIG. 6, the patient selects their own tooth shade 2 and this is displayed in box 8 of display box 4. In parallel, the MAT system measures the tooth shade 6 and the MAT generates a tooth shade map 10 for display in display box 4. The MAT also generates an image or picture of the patient's tooth for display 12 in display box 4. At this time, the dentist, preferably after discussion with the patient, selects a type of tooth whitening treatment 46 and inputs this information into a database 48 of treatments that uses a processor to predict the shade of patient's teeth after the whitening treatment. This information is then displayed 14 in display box 4. The prediction is achieved via an expert system that is produced by collecting and assembling in a database before and after tooth whitening images. This information can then be augmented by information such as the particular tooth whitening brand and tooth whitening procedure employed. Thus the map 14 produced would be determined by finding and analyzing those shade images in the database most closely matching the tooth shade map generated by the MAT system and the procedure parameters to the corresponding image in the database. The display box 4 also can display the corresponding image or picture 16 of the patient's tooth as it would look after a whitening procedure.

Once the procedure and the predictions are discussed with the patient, the dentist applies the tooth whitening procedure 18 to the patient. The patient's tooth is then measured on an MAT system 20 after the treatment. A display 22 then displays the tooth shade selected by the patient 24 (see also reference character 8), the tooth shade map generated by the MAT before treatment 30 (see also reference character 10), the image or picture of the patient's tooth before treatment 28 (see also reference character 12), the predicted shade map 30 (see also reference character 14) and the predicted image 32 (see also reference character 16). Additionally, the display 22 also displays a shade map 34 of the patient's natural tooth after the tooth whitening as generated in MAT step 20 and an image 36 of the patient's natural tooth after the tooth whitening procedure.

By comparing the images and shade maps in display 22, the dentist and the patient can then discuss whether further treatments are advisable 38. If not 40, the patient can return periodically to the dentist for further measurements to determine if the whitening has faded. If further treatments are advisable 42, the process can be repeated. In all events, the results 44 of the tooth whitening procedure are collected and used to augment database 48.

Also, because the morphology of teeth can impact their appearance, there is also provided in accordance with the present invention, a method to calibrate the MAT system for the differing morphology of teeth. More specifically, the method comprises:
 (a) measuring the tooth of interest using the system;
 (b) inspecting the morphology of the tooth and determining its location in the full arch, i.e., its tooth number;
 (c) inputting this information to either the database of a web site or an expert system; and
 (d) modeling or correcting differences in the interpretation of teeth based on the tooth morphology.

Thus, the effect of tooth shape or morphology on any subsequent tools that process the image (i.e. tooth whitening, shade expert, quality control, etc.) would be substantially reduced.

Crown Design: According to other aspects of the present invention, there are provided systems to assist laboratories in designing crowns, modifying the three-dimensional model of a tooth, and determining a recipe for building a particular prosthesis. This aspect of the present invention comprises two distinct processes. The first process is for obtaining a customized appearance map using a shade computer aided design software module. The dental technician then uses the customized appearance map as a reference when creating the restoration. The second process provides for obtaining a recipe for crown restoration wherein the dental technician creates a computerized crown model using a crown computer aided design software module. The crown model can then be used as a prescription for manufacturing the restoration.

The first process, appearance determination with shade computer aided design, is concerned with assisting the prosthesist or ceramist in obtaining a customized appearance map that better suits the users personal approach. MAT systems such as the commercially available ShadeScan System or the MAT system described hereinabove provide dental technicians with appearance information about the subject tooth in the form of two-dimensional maps representing the tooth surface. The maps indicate what is the closest shade of a given commercially-available shade guide for a given region of the tooth's surface. Therefore, these maps can be viewed as a mosaic of regions of different shades, conceptually similar to a paint-by-number template.

In many cases, however, the maps contain artifacts that either confuse the technician or are simply undesirable. For example, the map may contain a proportionally very small area of a specific shade X within a larger area of another shade Y. It may be clear to the technician that the area of shade X will have little or no impact on the outcome. Another example might involve artifacts on the tooth. The natural tooth needing to be replaced may have artifacts such as cracks, calcifications or dark spots that the technician may not wish to reproduce in order to improve overall aesthetics.

Prior art MAT systems provide no means of adjusting the appearance map to fit the user's need. Thus, the present invention solves a long felt need in the art by providing such a means.

Figure 7:
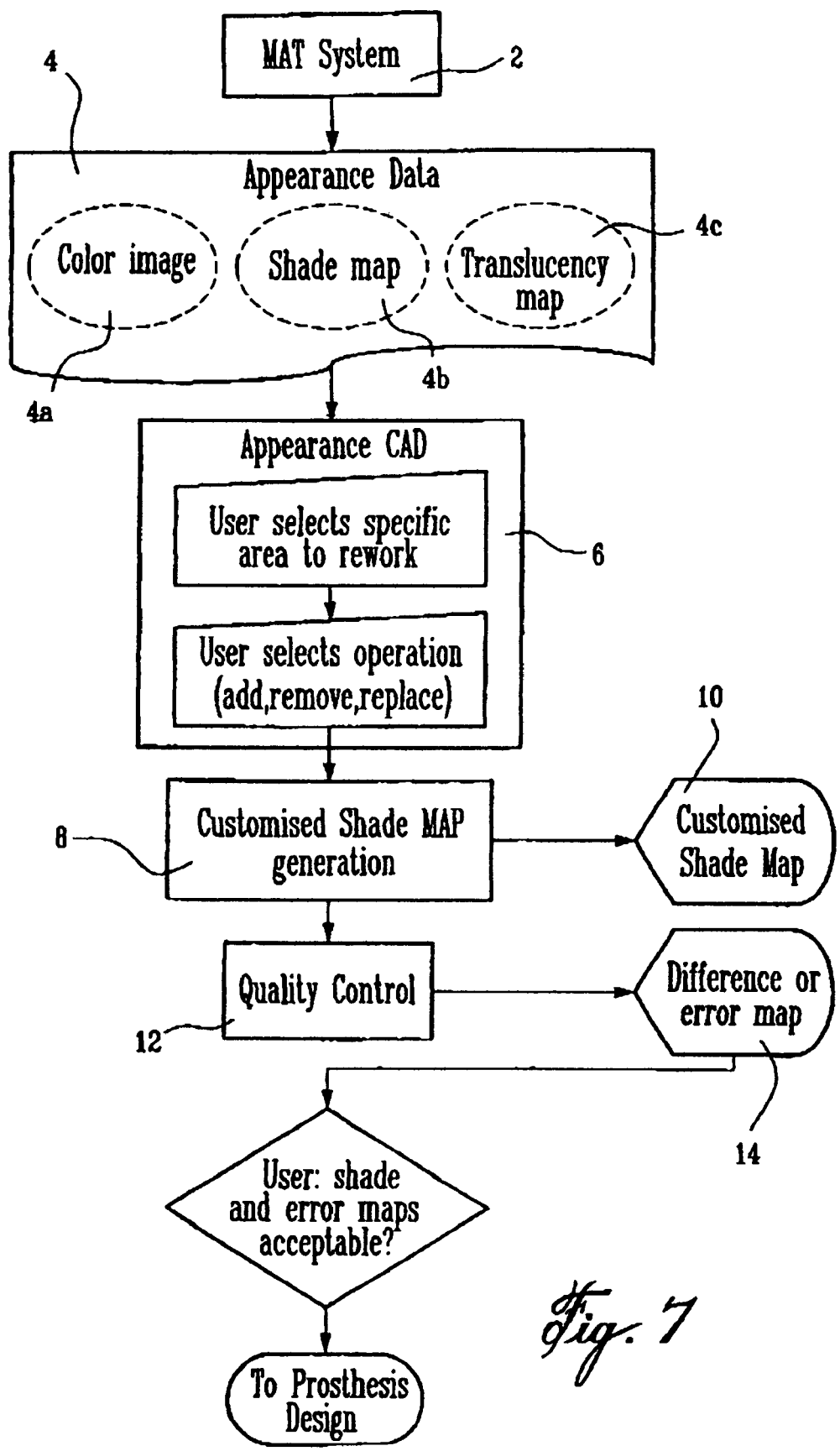
FIG. 7 is a flow chart outlining a preferred appearance determination with shade computer aided design aspect of the present invention.

FIG. 7 illustrates the shade computer aided design process. In the preferred embodiment of the invention, the MAT system 2 is used to obtain appearance data 4 advantageously composed of, but not limited to a color image of the tooth 4a, a shade map 4b and a translucency map 4c. The appearance data 4 is then fed to the appearance computer aided design module 6. It is within this module that the technician is allowed to manipulate the shade map.

The contemplated manipulations include one or more of: (i) selecting a region by clicking on it, or by using drawing tools to outline the desired region, such tools being similar to those found in commercially available computer drawing packages such as Adobe® Illustrator; (ii) removing regions of specific shade with the software automatically assigning the same shade to the removed region as the region surrounding the removed region; (iii) adding new regions to replace all or part of an existing region, the user specifying the shade the new region should be; and/or (iv) replacing existing regions by changing only the indicated shade, based upon the user's choice.

The appearance computer aided design module 6 assists the user by proposing a choice for each possible manipulation. For example, when a region is removed, the module 6 automatically finds the shade of the surrounding region and assigns this shade to the region that was removed. When a new region is added, the module 6 infers what is the best overall choice for this new region and proposes it to the user.

Whenever a manipulation is effected by the user in the module 6, a copy of the original shade map is customized 8 and displayed to the user 10. In parallel, the new customized map is also compared to the measured color information of the natural tooth 12 in order to obtain a difference or error map 14. The error map 14 indicates to the user what is the "cost" of each manipulation, i.e., how it affects the aesthetics. For example, removing a specific region on the shade map may cause the error map to show that the natural tooth differs strongly from the customized appearance map. Conversely, the user can then use this feedback to manipulate the appearance map iteratively until the error map shows no significant difference in appearance with the natural tooth. The comparison process is identical to that used for the MAT system's quality control module.

As an alternative embodiment of the invention, the user also has the option to start with a blank shade map. At this stage, the error map is obviously indicating a large appearance differential everywhere on the tooth. The user then adds regions one by one and by trial and error, and with the assistance of the module 6 as described above, iteratively obtains a shade map that corresponds to the user's needs.

The second process of this crown design embodiment of the present invention, occurs when the dental technician already knows what appearance he wishes to achieve for the restoration. Traditionally, the technician then proceeds directly to manufacture the restoration, using his skill and know-how to infer what materials and techniques will achieve the best results in terms of cost and aesthetics. According to the present invention, the technician instead uses virtual tools that mimic the behavior of the traditional tools to create a computerized model of the crown.

In the current state of the art, dental technicians have no objective way to predict what their restoration work will look like before the work is actually completed. The technician is responsible for inferring all of the manufacturing parameters, according to his skill and know-how. These parameters include: the coping material (e.g. titanium, zircon, gold), sure (or body) material (e.g. fused porcelain ceramics, composites), the volume available for applying the materials, and the method used to assemble the materials together to make them into a crown. In addition, the set of parameters may include for example the oven time for a fused porcelain crown. The various parameters for crown manufacturing are well known to those ordinarily skilled in the art.

In solving the long felt problems of the art, the crown computer aided design module of the present invention provides dental technicians with a computerized model of the crown, giving the technicians the ability to predict the outcome of a particular choice of manufacturing parameters. Although, this section of the detailed description refers specifically to crowns, the process can also apply to other types of restorations such as, but not limited to, bridges.

Figure 8:
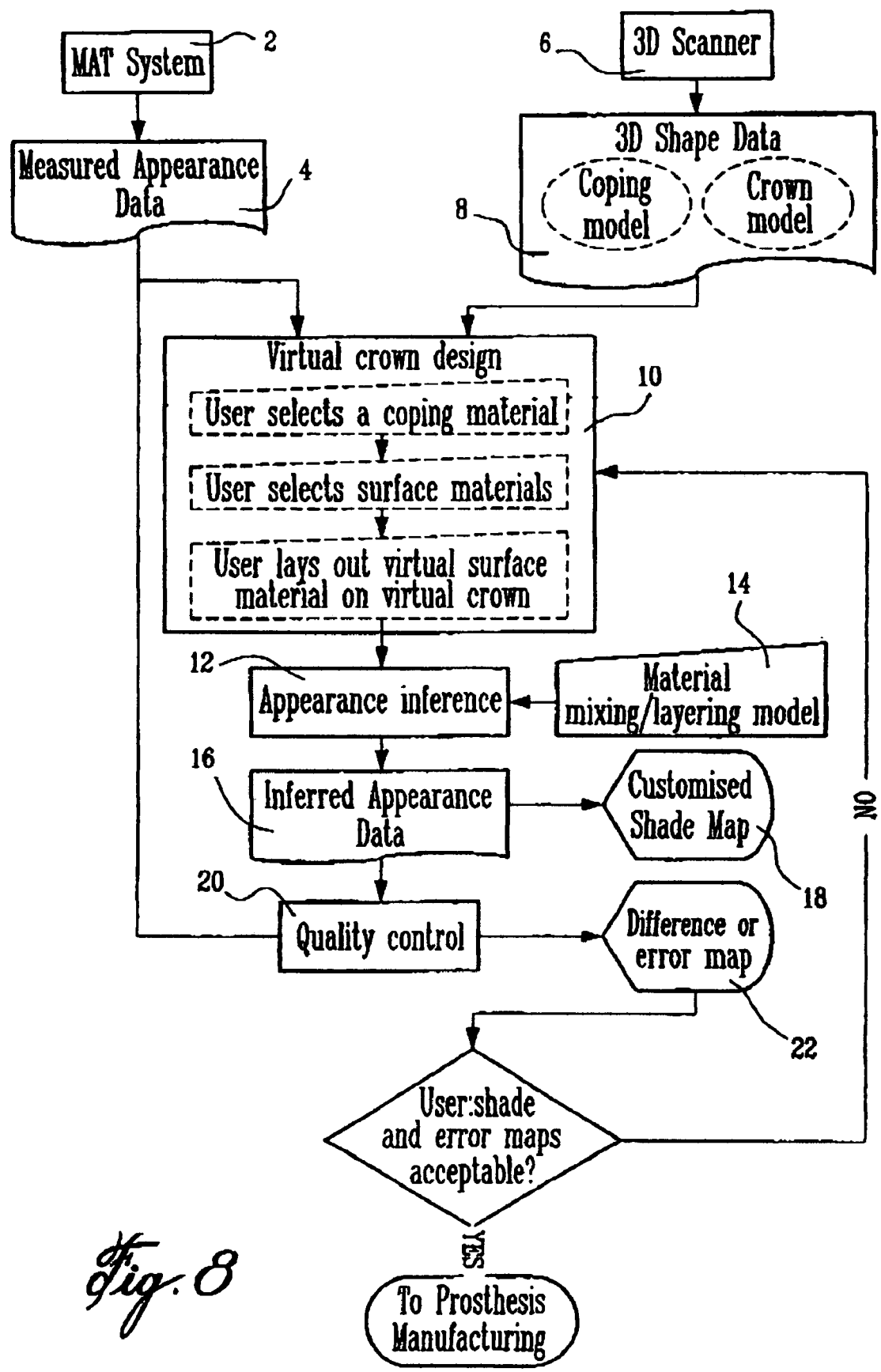
FIG. 8 is a flow chart outlining a preferred crown design embodiment of the present invention.

Referring to FIG. 8, a MAT system 2 generates appearance data 4 according to the measurement it makes of the natural tooth. In parallel, a 3D scanner system 6, such as the Pro-50 system, is used to obtain three-dimensional shape information 8 about the restoration. Typically, but not always, such systems provide a three dimensional model of the stump, coping and crowns suitable for computer-assisted manufacturing (e.g. automated milling machines).

The appearance information 4 and the three dimensional shape data 8 are then fed to the virtual crown design module 10. Within this module 10, the user sets the various parameters that are necessary to complete the virtual crown, using software tools that mimic the traditional tools of the trade. Advantageously, CAD drafting tools generally available in commercial CAD packages (e.g. AutoCADS) are also provided. At a minimum, the coping and body materials have to be specified, and the layers of body material have to be accurately described (location, thickness, color, mix). The virtual crown model is augmented and updated as the user manipulates these parameters.

The crown model is then used by the appearance inference module 12, which makes use of a material mixing and layering model 14. This layering model describes how materials interact together to create a given appearance, information that is generally provided by manufacturers of commercially available dental restoration materials for their own products. The mixing and layering model advantageously accesses a database that contains this information. The appearance inference module 12 then generates new appearance data 16 that corresponds to what the crown would look like to the MAT system if it were manufactured. The inferred appearance is then displayed to the user in the familiar form of a shade map 18, and is used together with the measured appearance data in the quality control module 20 to obtain a difference or error map 22, consistent with what was previously described above for the shade computer aided design system. The user can then iterate through the process, adding, removing or replacing materials of the virtual crown, until the user is satisfied with the result.

Although the present invention has been described in the context of dentistry, it is believed that those of ordinary skill in the art will be able to make obvious modifications of the above-described systems and methods for application in other contexts or domains, such as, but not limited to, cosmetic skin analysis and the pulp and paper field.

Indeed, the problem that a dentist has in selecting a cosmetically pleasing dental restoration has an analogue, for example, at the cosmetic counter of any department store. When a woman purchases makeup it is often difficult to find a foundation that is right for her skin. This is further complicated as a person's tan changes with the seasons. Furthermore, there is a plethora of eye shadows, eyeliner, mascara, lipstick, etc. from which to choose to enhance the skin and physical features. Again, these colors are constantly changing with the latest styles and fashion.

Technically, the problem of matching skin tone is less challenging than that of matching teeth. Note that skin is far less translucent than teeth and one is not interested in capturing isolated artifacts when dealing with skin. A device can therefore be developed that takes an image of the person's skin and determines the person's exact skin tone. This information could even be sent directly to the production plant to determine an exact match for the person's tan—in essences a customized makeup. Such a product could be installed in stores (not the possibilities for a pay-per-use system: a marketing and communication tool for the cosmetic production source). It could also be extended with the unit given to individuals for use at home in return for a commitment and eventually it could be sold to individuals.

The device could also be given to individuals for use at home and they could purchase their makeup via a dedicated web site—with a client committing itself to a minimum annual purchase of cosmetics. The dedicated web sit could be a cosmetic and fashion clearing house, also providing information and products from other cosmetic and fashion related businesses.

For example, if a person transmitted his skin color information to the web-site, he or she could click on an icon from a fashion magazine that would recommend certain "in" eye shadow shades. This technology could be licensed to a number of cosmetic manufacturers.

Although the present invention has been described hereinabove by way of preferred embodiments thereof, it can be modified without departing from the spirit and nature of the subject invention as defined in the appended claims.

The above-mentioned patents, patent applications and articles are hereby incorporated by reference in their entirety.

The invention claimed is:

1. A device for measuring an appearance of an object that is based on a digital camera platform design, said device comprising:
    (a) a color sensor for capturing an image of an object and collecting appearance data from said object;
    (b) a memory storage system for saving said captured image;
    (c) a display on said device for displaying the captured image; and
    (d) a CPU internal to said device allowing interpretation and processing of said appearance data to determine appearance factors for said image.

2. A device as defined in claim 1 that is a haudheld device.

3. A handbeld MAT device as defined in claim 2, wherein said device comprises a means for calibrating said device, said calibration means comprising one or more of;
   (a) a cradle for holding the MAT device, said cradle housing designed to accurately position a calibration target correctly for the MAT device
   (b) providing a calibration process with a sleep mode;
   (c) spatial compensation means for known and consistent spatial variations in the image;
   (d) light feedback control means using camera output to modify a light source;
   (e) means for implementing the concept of absolute color standards for inter-device communication;
   (f) process for selecting reference colors of a calibration standard; and/or
   (g) means (or signaling need for replacement of calibration color patch.

4. A device as defined in claim 3 wherein said cradle fits over a nose of said device and serves as a stand for the device.

5. A device as defined in claim 3 wherein either said device or said cradle is provided with a proximity switch for automatically starting the calibration device when the device is placed in the cradle and/or automatically stopping the calibration device when the device is removed from the cradle.

6. A device as defined in claim 3 wherein said device is provided with a calibration target; said calibration target mounted in a spring loaded door located over an exit of said handheld device.

7. A device as defined in claim 6 further comprising an asceptic shield provided with a tongue means for pushing open said door when the shield is placed over a nose of the device.

8. A device as defined in claim 6 wherein said calibration target is mounted on a rear of said door.

9. A device as defined in claim 6 further comprising a proximity sensor mounted in the handpiece to detect when the door is fully closed.

10. A device as defined in claim 3 wherein said sleep mode comprises means for changing an illumination intensity if the unit has not been used far a set period of time.

11. A device as defined in claim 3 wherein calibration patch is provided with bar codes for identifying the calibration patch.

12. A computer aided shade design process wherein a MAT system is as defined in claim 1.

13. A computer aided dental restoration design process wherein a MAT system is as defined in claim 1.

14. A device as defined in claim 1, wherein said sensor for capturing the image is selected from a group comprising of a CMOS sensor, a CCD sensor, and an X3 sensor based on color separation properties of silicon.

15. A device as defined in claim 1, wherein said display device comprises an LCD panel.

16. A device as defined in claim 15, wherein said LCD panel is able to display interpretive maps of the captured image.

17. A device as defined in claim 1, wherein said object is a dental object.

18. A device as defined in claim 17, wherein said dental object comprises one of a crown, plate, bridge and replacement tooth.

19. A device as defined in claim 1, further comprising a microphone to record voice information to describe and/or annotate the captured image of the object.

20. A device as defined in claim 19, wherein said CPU processor links said captured image of the object with said recorded voice information describing and/or annotating said captured image of the object.

21. A device as defined in claim 20 further comprising an internal speaker to play the recorded attached voice annotations.

22. A device as defined in claim 1 further comprising a keypad for inputting textual information about the image of the object.

23. A device as defined in claim 22 wherein said CPU processor links said textual information with said image of the object.

24. A device as defined in claim 1 further comprising a means for illuminating said object.

25. A device as defined in claim 24 wherein said illumination means comprises white light emitting diodes.

26. A device as defined in claim 1 further comprising a means for altering an illumination pattern and depth of focus attached on a front portion of said device.

27. A device as defined in claim 1 wherein said CPU comprises means for connecting to and communicating with a computer network.

28. A device as defined in claim 27 wherein said computer network is the Internet.

29. A device as defined in claim 27 wherein said CPU transmits said image of said object to said computer network.

30. A device as defined in claim 27 wherein said CPU receives software updates and enhancements from said computer network.

31. A device as defined in claim 27 wherein said CPU receives information regarding maintenance check ups and device problem diagnoses from said computer network.

* * * * *